(12) United States Patent
Blick et al.

(10) Patent No.: US 8,217,665 B2
(45) Date of Patent: Jul. 10, 2012

(54) RADIO-FREQUENCY ION CHANNEL PROBE

(75) Inventors: Robert H. Blick, Madison, WI (US); Hua Qin, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 675 days.

(21) Appl. No.: 12/277,837

(22) Filed: Nov. 25, 2008

(65) Prior Publication Data

US 2010/0127716 A1 May 27, 2010

(51) Int. Cl.
*G01R 27/26* (2006.01)
*A61K 9/127* (2006.01)
(52) U.S. Cl. ........................................ 324/675; 424/450
(58) Field of Classification Search .................. 324/675
See application file for complete search history.

(56) References Cited

U.S. PATENT DOCUMENTS

| 5,189,713 | A  | * | 2/1993  | Shaw ................................ 385/2 |
| 6,493,288 | B2 | * | 12/2002 | Khuri-Yakub et al. ........ 367/181 |
| 6,501,414 | B2 | * | 12/2002 | Arndt et al. ..................... 342/22 |
| 6,945,115 | B1 | * | 9/2005  | Wang ............................... 73/718 |
| 7,125,528 | B2 | * | 10/2006 | Besecker et al. ............. 422/211 |
| 7,358,077 | B2 | * | 4/2008  | Zimmermann et al. ... 435/285.2 |
| 2002/0053915 | A1 | * | 5/2002  | Weaver et al. ................ 324/600 |

* cited by examiner

*Primary Examiner* — Jeff Natalini
(74) *Attorney, Agent, or Firm* — Boyle Fredrickson, S.C.

(57) ABSTRACT

A patch-clamp system employs a high-frequency characterization of cell wall membranes. Changes in the frequency response of a tank circuit incorporating the cell wall membrane impedance provides highly sensitive and highly time-resolved measurements of ion channel activity.

20 Claims, 3 Drawing Sheets

RADIO-FREQUENCY ION CHANNEL PROBE

STATEMENT REGARDING FEDERALLY SPONSORED RESEARCH OR DEVELOPMENT

—

CROSS REFERENCE TO RELATED APPLICATION

—

BACKGROUND OF THE INVENTION

The present invention relates to a "patch-clamp" for investigating ion transport through cellular membranes and in particular to a patch-clamp system that may provide real-time tracing of ion channel activity with a bandwidth of up to 500 MHz.

The lipid bilayers that make up cell membranes include ion channels that control the flow of ions into and out of cells. Certain ion channels open in response to signaling molecules including naturally occurring signaling molecules and drug molecules. In the development of therapeutic drugs it is necessary to determine the effect of the drug on ion channels either to avoid adverse effects or to create a positive therapeutic effect for the treatment of ion-channel related diseases.

Analysis of the response of ion channels may be conducted with a so-called "patch-clamp", traditionally a micropipette adhered to the surface of a cell by a slight suction. An electrical connection across the membrane of the cell is then made by one of a number of techniques, for example, by applying a sharp suction pulse to the pipette to open a hole in the cell wall. Measurement of small electrical changes across the cell membrane made by a miniature electrode inserted into or near the opening may then be used to deduce the flow of ions through the ion channels. The small amounts of electrical current involved in these measurements require an extremely high resistance seal between the pipette and the cell wall (a giga-ohm seal).

Drug screening often requires making many ion-channel measurements. Accordingly the pipette having a single opening has been replaced with a plate having multiple small pores each of which may accept a cell. The plate array allows the parallel processing of multiple cells and may be more readily integrated into automated equipment.

The sensitivity of measurements of small current flows through ion channels is significantly limited by the poor electrical characteristics of a bare electrode immersed in the aqueous medium inside or outside of the cell. As a result, rapid changes in ionic transport cannot be resolved in the time domain.

SUMMARY OF THE INVENTION

The present invention provides a high-frequency measurement of cell wall impedance changes due to ion channel activity. This differs from the typical "direct current" measurements of currents or voltages adopted in the prior art. By construction of a "tank circuit" incorporating the impedance of the cell membrane, changes in the resonance of this tank circuit may be used to accurately and quickly assess changes in the cell wall membrane. The high-frequency measurements allow electrodes to be formed as waveguides having far higher sensitivity and response rates than a bare electrode immersed in aqueous medium.

Specifically the present invention provides a high frequency patch-clamp system using an electrically insulating support providing support region for holding a cellular membrane fixed with respect to the electrically insulating support. A first and second electrode on opposite sides of the support region, separated by the cellular membrane, are connected to circuitry providing a high-frequency signal across the first and second electrodes to determine changes of impedance across the cellular membrane from measurement of a change in electrical resonance. It is thus one object of at least one embodiment of the invention to employ an alternating current measurement technique to improve the sensitivity of ion channel measurements. It is another object of the invention to eliminate the need for manipulation of freestanding electrodes during the patch-clamp process.

The support region may be an aperture through the electrically insulating support forming a lip on a first side of the aperture sized to accept a cellular membrane spanning the lip to form a giga-ohm seal with the electrically insulating support.

It is thus an object of the invention to permit both AC and DC measurements, the latter employing the aperture.

At least one of the first and second electrodes may be a waveguide attached to the electrically insulating support.

It is thus an object of at least one embodiment of the invention to permit waveguide-like electrodes to provide a high-frequency response.

The waveguide may be a strip-line.

It is thus an object of at least one embodiment of the invention to provide a waveguide that may be readily fabricated on an insulating substrate.

The circuitry may be a tank circuit incorporating a capacitance across the cellular membrane as a capacitance of the tank circuit.

It is thus another object of the invention to provide a simple method of measuring impedance changes across a cellular membrane by monitoring a tank circuit resonance.

The circuit includes at least one inductor in series with a capacitance.

It is thus an object of at least one embodiment of the invention to provide a simple method of tuning the tank circuit for convenient measurement.

The electrically insulating support may be a planar support and includes multiple apertures and lips each associated with a least one different second electrode for parallel measurements of cellular membranes at each of the multiple apertures.

It is thus an object of at least one embodiment of the invention to provide a system suitable for high throughput measurement.

The high-frequency signal may be in excess of one MHz.

It is thus an object of at least one embodiment of the invention to permit measurement of extremely small impedance values.

The impedance measured may be capacitance of the cellular membrane.

It is thus an object of at least one embodiment of the invention to permit measurement of membrane capacitance in lieu of current or voltage transfer.

Alternatively, the impedance measured may be resistance of the cellular membrane.

It is thus an object of at least one embodiment of the invention to permit conventional current flow measurements as manifest in resistance.

The first electrode may include two separated portions wherein the high-frequency signal is applied to one portion and monitored at the second portion.

It is thus an object of at least one embodiment of the invention to permit either reflected or transmitted energy measurements or both to be made.

These particular features and advantages may apply to only some embodiments falling within the claims and thus do not define the scope of the invention.

DETAILED DESCRIPTION OF THE PREFERRED EMBODIMENT

Figure 1:
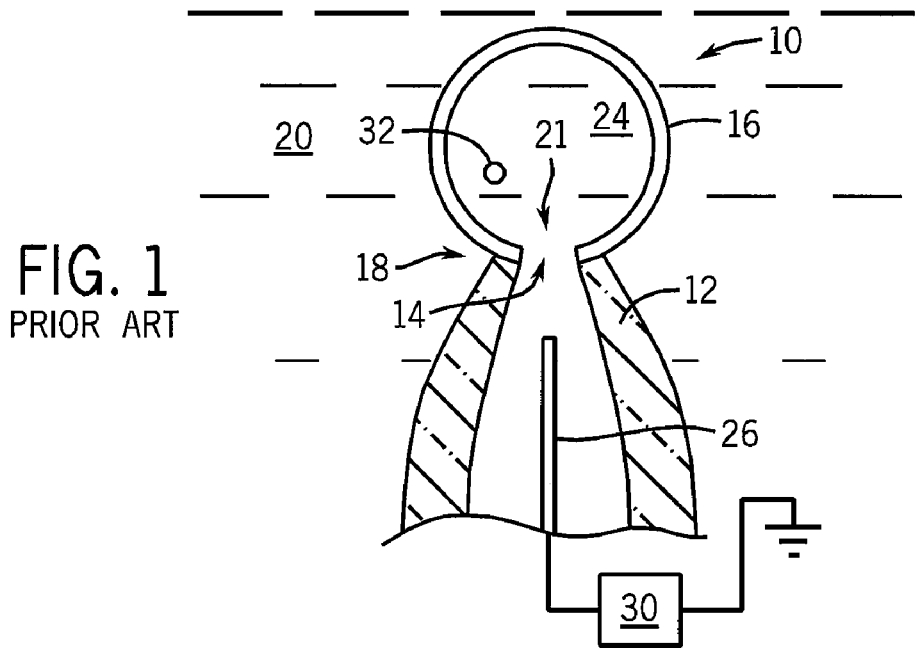
FIG. 1 is an elevational cross-section of a prior art patch-clamp used for whole-cell recording.

Referring now to FIG. 1, a prior art whole-cell patch-clamp 10 may employ a micropipette 12 having an aperture 14 to which a cell 16 is drawn by suction. The cell 16 may attach to the aperture 14 to create a giga-ohm seal to a lip 18 of that aperture. The cell 16 may otherwise be suspended in a liquid medium 20 providing an environment desired for a particular experiment.

A sharp suction may be used to open a hole 21 in the cell wall of the cell 16 providing a low resistance path from the interior cytoplasm of the cell through a solution 24 to a microelectrode 26 within the micropipette 12. The microelectrode 26 is typically a silver electrode coated with silver chloride for electrochemical stability.

A sensitive current detector 30 may be connected between the microelectrode 26 and the liquid medium 20 to measure the passage of ions 32 through channels in the cell wall. The current detector 30 may provide for a voltage-clamping action, if desired, using a conventional voltage feedback circuit. Generally the bare microelectrode 26 provides electrical characteristics that severely limit the frequency of the measure of ionic currents. Further, only resistive impedance of the cell wall may be determined.

Figure 2:
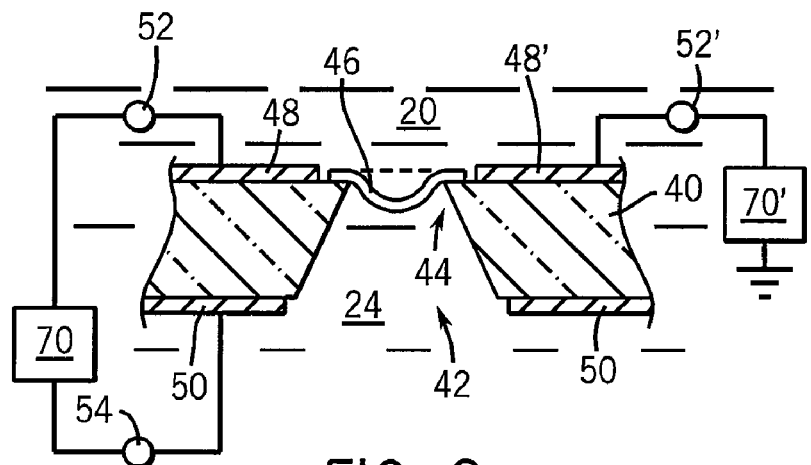
FIG. 2 is an elevational cross-section of a planar patch-clamp implementing the present invention allowing reflected or transmitted energy measurement.

Referring now to FIG. 2, the present invention provides an insulating substrate 40 having an aperture 42 providing a lip 44 on one side of the substrate 40 that may be spanned by a cellular membrane 46, for example, using the whole cell technique described above, or by a variety of other techniques well known in the art. A first electrode 48 may be positioned on one side of insulating substrate 40 and lip 44 while a second electrode 50 may be positioned on the other side of the insulating substrate 40 and lip 44 so that the first electrode 48 and second electrode 50 are on opposite sides of the cellular membrane 46. Each of electrodes 48 and 50 may connect via terminals 52 and 54 to measurement circuitry 70 that will apply a high-frequency signal across electrodes 48 and 50.

An additional first electrode 48' may also be positioned on the same side of the substrate 40 as electrode 48 to join thereto at the lip 44 but to extend to a second terminal 52' at which transmission through the network may be measured as will be described.

Electrode 50 may communicate with a solution 24 supporting the underside of the cellular membrane 46 and may for example be a silver/silver-chloride electrode of a type known in the art to minimize artifacts created by oxidation-reduction reactions at the metallic surface. As such, electrode 50 will be considered ground for the purpose of discussion.

Electrodes 48 and 48', where they contact the liquid medium 20, may also be silver/silver-chloride material; however, in the preferred embodiment, for most of their lengths they may be insulated from the liquid medium 20 and, in this insulated portion, electrodes 48 and 48' may preferably be a micro-strip-line having a controlled and well-defined electrical characteristic such as will provide a waveguide for high frequency transmission of electrical signals. Such micro-strip-lines may, for example, provide a conductor sandwiched between a well-characterized dielectric in turn sandwiched between ground planes to provide the necessary boundary conditions for waveguide propagation. The fabrication of the micro-strip-lines may be made by using well-known integrated circuit techniques or surface coating methods.

Figure 3:
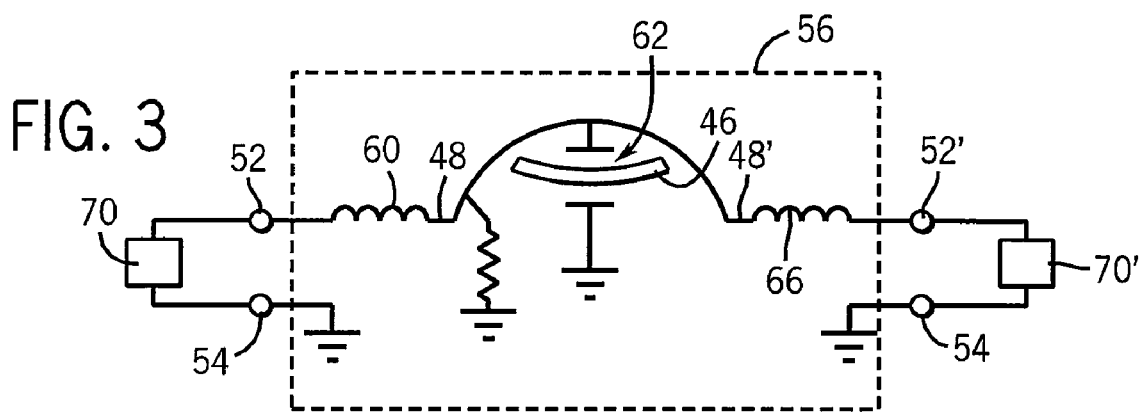
FIG. 3 is a schematic representation of a four-port tank circuit implemented using the patch-clamp of FIG. 2.

Referring now to FIG. 3, the device of FIG. 2 provides a four terminal network 56 in which terminal 52 and terminal 54 provide input terminals for application of a radiofrequency signal (for example, on the order of 100 MHz) and optional measurement of reflected energy, and terminal 52' and 54 provide output terminals for measurement of transmitted energy.

Terminal 52 may lead to electrode 48 through an inductor 60 being preferably a discreet inductor (for example, on the order of 20 nH) but possibly being formed by the length of electrode 48 itself which may be used to tune the tank circuit as will be described. Electrode 48 may in turn connect to ground (50) through a coupling capacitive 62 through the cellular membrane 46 and through a small resistance 64 representing the giga-ohm seal between the substrate 40 and the cellular membrane 46 and a parallel resistive component through the cellular membrane 46.

The junction of electrode 48 and capacitance 62 is also connected with electrode 48 which may then join with an inductor 66 which leads to terminal 54.

The circuit so described will be recognized as a tank circuit providing for series resonance between the inductors 60 and capacitance 62. This resonance may be measured between terminals 52 and 54 as a reflected energy by measurement circuitry 70 or between terminals 52' and 54 as a transmitted energy by measurement circuitry 70'. Such analyzers may, for example, provide for a frequency sweep measuring reflected or transmitted energy or may provide for parallel resonance measurements by broadband excitation and frequency analysis for using the fast Fourier transform or other similar technique.

Figure 4:
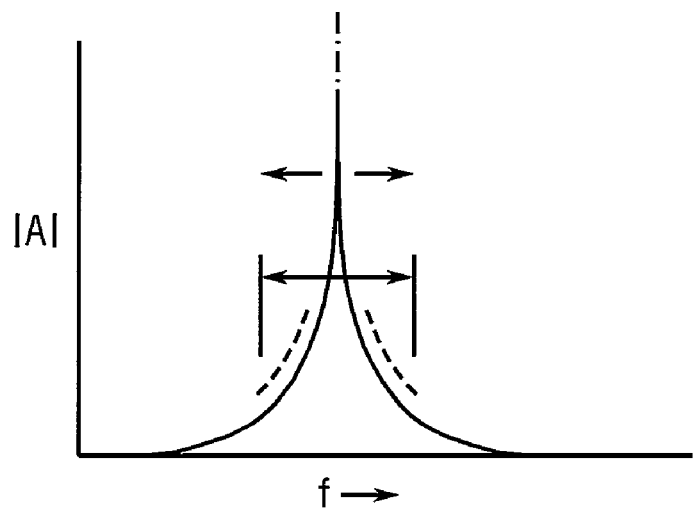
FIG. 4 is the plot of a frequency resonance of the tank circuit of FIG. 3, measurable in the present invention to determine capacitive or resistive impedance across the cell membrane.

Referring now to FIG. 4, the measured resonance 72 will show an amplitude (power, voltage, current) as a function of frequency having a peak at a center frequency 74 determined by the inductance 60 and capacitance 62, and having a width 76 ($Q=f/\Delta f$) determined by the resistance and dielectric losses 64. As will be understood in the art, changes in the capacitance 62 will be reflected in movement of the center frequency 74 of the resonance 72 by a frequency shift whereas changes in the resistance 64 will be reflected in changes in the width 76 of the resonance 72.

Monitoring the resonance 72 will provide extremely high time resolution of ion transfer events through the cellular membrane 46. Either or both of resistance and capacitance can be measured in this manner and it will be understood that a selection of component values of the inductors 60 and 66 and capacitance 62 (the latter which may be controlled through the selection of aperture size) can be used to accentuate one or the other of these measurements.

Figure 5:
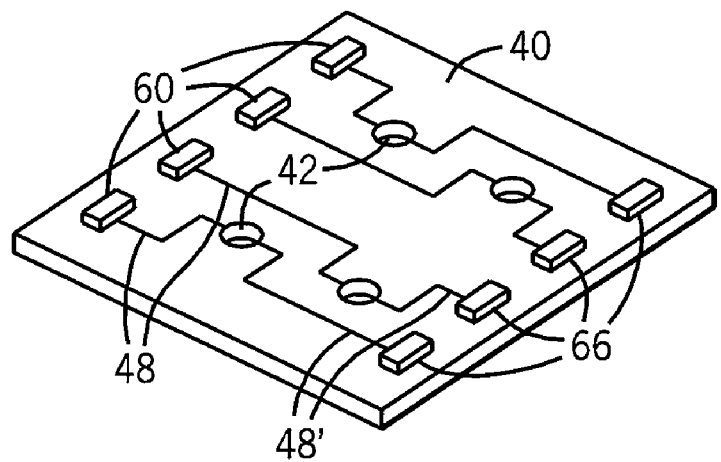
FIG. 5 is a perspective view of a multiport planar patch-clamp system using the present invention.

Referring now to FIG. 5, the substrate 40 may include multiple apertures 42 each having a dedicated set of electrodes 48 and 48' to permit high throughput analysis of multiple cells at each of the apertures 42. The inductors 60 and 66 may be discrete inductors placed on the surface of the substrate 40 using conventional electrical assembly techniques.

Figure 6:
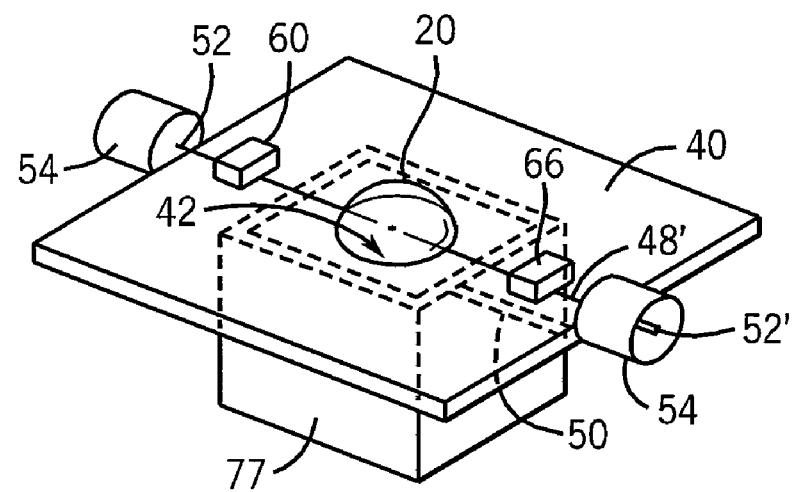
FIG. 6 is a perspective view of an experimental apparatus implementing the present invention and FIG. 7 is a figure similar to that of FIG. 2 showing patch-clamp of the present invention applied to an intact cell membrane.

Referring now to FIG. 6, terminals 54 and 52 may be implemented through a standard high-frequency coaxial connector as may terminals 52' and 54. The impedance of the micro-strip-lines may be set to approximate a standard impedance of approximately 50 ohms to provide impedance matching with subsequent measurement circuitry 70 and with the tank circuit by proper selection of the component values and device dimensions and/or the use of matching networks (not shown).

A chamber 77 of solution may be placed underneath the substrate 40 and connected to the electrodes 50 on the underside of substrate 40. Liquid medium 20 may be limited in extent about the aperture 42 to limit its effect on the transmission of high-frequency signals through electrodes 48 and 48'.

Figure 7:
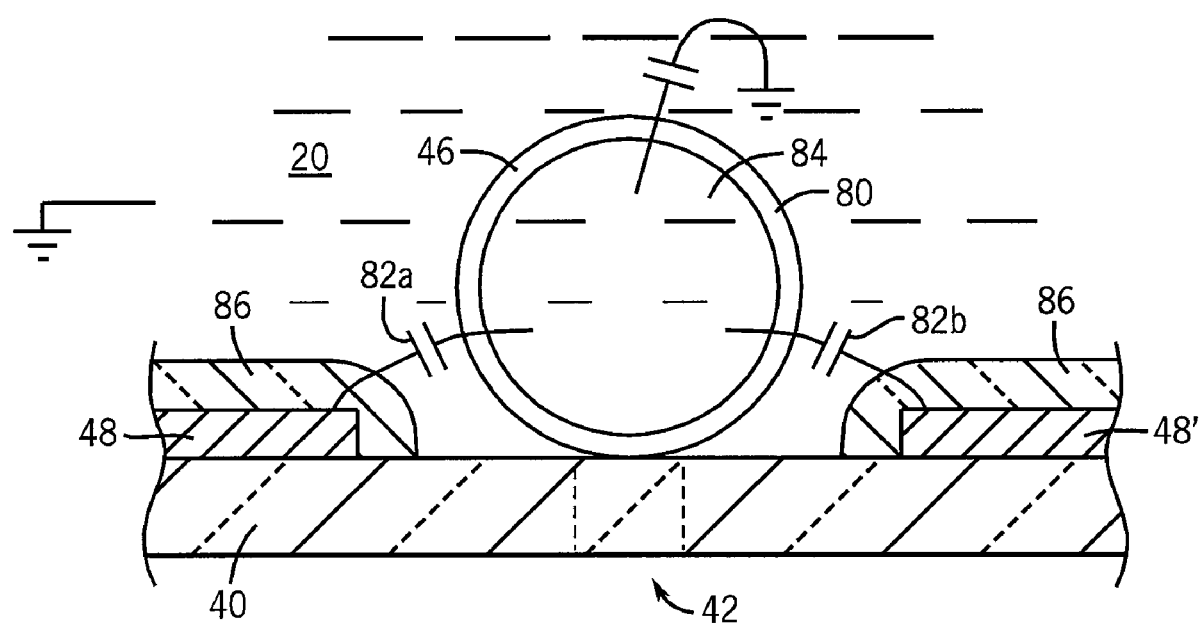

Referring now to FIG. 7, if simultaneous DC and AC measurements through the cellular membrane 46 are not required (such as can be conducted using the system of FIG. 2), the present invention can be used with an intact cell 80 resting on the insulating substrate 40 without an aperture 42 (or with an optional aperture 42 only used to stabilize the cell 80 with a slight negative pressure). In this case, the measurement is an AC measurement of series capacitance 82a and 82b, the first from electrode 48 through the cellular membrane 46 into the cellular fluid 84 and the second from the cellular fluid 84 through the cellular membrane 46 to electrode 48'. As shown in this figure, normally the electrodes 48 will be covered with a dielectric layer 86 separating them from the liquid medium 20 to eliminate resistive mode conduction.

It is specifically intended that the present invention not be limited to the embodiments and illustrations contained herein, but include modified forms of those embodiments including portions of the embodiments and combinations of elements of different embodiments as come within the scope of the following claims.

We claim:

1. A high frequency cell membrane analyzer for cellular membranes of lipid bilayer with ion channels, the analyzer comprising:
    an electrically insulating support adapted to provide a support region for holding the cellular membrane fixed with respect to the electrically insulating support;
    a first and second electrode on opposite sides of the support regions separated by the cellular membrane; and
    circuitry providing a high-frequency signal across the first and second electrodes and determining changes of impedance across the cellular membrane from measurement of a change in electrical resonance and providing a measureable output indicating the determined change in impedance.

2. The high frequency cell membrane analyzer of claim 1 wherein the support region is an aperture through the electrically insulating support forming a lip on a first side of the aperture sized to accept a cellular membrane spanning the lip to form a giga-ohm seal with the electrically insulating support.

3. The high frequency cell membrane analyzer of claim 1 wherein at least one of the first and second electrodes is a waveguide attached to the electrically insulating support.

4. The high frequency cell membrane analyzer of claim 3 wherein the waveguide is a strip-line.

5. The high frequency cell membrane analyzer of claim 1 wherein the circuitry is a tank circuit incorporating a capacitance across the cellular membrane as a capacitance of the tank circuit.

6. The high frequency cell membrane analyzer of claim 1 wherein the circuit includes at least one inductor in series with a capacitance.

7. The high frequency cell membrane analyzer of claim 1 wherein the electrically insulating support is a planar support and includes multiple apertures and lips each associated with a least one different second electrode for parallel measurements of cellular membranes at each of the multiple apertures.

8. The high-frequency cell membrane analyzer of claim 1 wherein the high-frequency signal is in excess of one MHz.

9. The high frequency cell membrane analyzer of claim 1 wherein impedance measured is capacitance of the cellular membrane.

10. The high frequency cell membrane analyzer of claim 1 wherein the impedance measured is resistance of the cellular membrane.

11. The high-frequency cell membrane analyzer of claim 1 wherein the first electrode includes two separated portions and wherein the high-frequency signal is applied to one portion and monitored at the second portion.

12. A method of measuring ion transport through a cellular membrane of lipid bilayer with ion channels, the method comprising the steps of:
    (a) placing the cellular membrane to span a lip formed on an insulating substrate so that the lip and membrane separate a first and second electrode on opposite sides of the lip;
    (b) applying a high-frequency electrical signal across the electrodes to determine an impedance therebetween; and
    (c) monitoring changes in the impedance to detect ionic transport through the cellular membrane for events having a time resolution of substantially less than 20 μs.

13. The method of claim 12 wherein the impedance is determined by monitoring the electrical resonance of a tank circuit formed of inductors in the electrodes.

14. The method of claim 13 wherein the impedance is determined by a reflection from the tank circuit at the first and second electrode.

15. The method of claim 13 wherein the first electrode has a first and second portion and impedance is determined by a transmission of the tank circuit from a first portion of the first electrode to a second portion of the first electrode.

16. The method of claim 13 wherein the impedance is determined by a shifting of a natural resonance of the tank circuit in frequency.

17. The method of claim 13 wherein the impedance is determined by a broadening of a natural resonance of the tank circuit in frequency.

18. The method of claim 12 wherein the high-frequency signal is in excess of 1 MHz.

19. The method of claim 12 wherein impedance measured is capacitance of the cellular membrane.

20. The method of claim 12 wherein the impedance measured is resistance of the cellular membrane.

* * * * *